United States Patent
Irie et al.

(10) Patent No.: US 10,865,428 B2
(45) Date of Patent: Dec. 15, 2020

(54) METHOD FOR PRODUCING ORGANIC ACID

(71) Applicant: KAO CORPORATION, Tokyo (JP)

(72) Inventors: Yutaka Irie, Wakayama (JP); Shingo Koyama, Wakayama (JP)

(73) Assignee: KAO CORPORATION, Tokyo (JP)

( * ) Notice: Subject to any disclaimer, the term of this patent is extended or adjusted under 35 U.S.C. 154(b) by 229 days.

(21) Appl. No.: 16/065,638

(22) PCT Filed: Dec. 22, 2016

(86) PCT No.: PCT/JP2016/088288
§ 371 (c)(1),
(2) Date: Jun. 22, 2018

(87) PCT Pub. No.: WO2017/110970
PCT Pub. Date: Jun. 29, 2017

(65) Prior Publication Data
US 2019/0300915 A1    Oct. 3, 2019

(30) Foreign Application Priority Data
Dec. 24, 2015 (JP) ................... 2015-251574

(51) Int. Cl.
*C12P 7/46* (2006.01)
*C12R 1/845* (2006.01)

(52) U.S. Cl.
CPC ............. *C12P 7/46* (2013.01); *C12R 1/845* (2013.01)

(58) Field of Classification Search
None
See application file for complete search history.

(56) References Cited

FOREIGN PATENT DOCUMENTS

| JP | 3-505396 A | 11/1991 |
|---|---|---|
| JP | 6-153970 A | 6/1994 |
| JP | 2000-37196 A | 2/2000 |
| JP | 2000037196 A * | 2/2000 |
| WO | WO 90/00199 A1 | 1/1990 |

OTHER PUBLICATIONS

Fu, Y.-Q. et al., Appl. Biochem. Biotechnol. 2010 vol. 162, pp. 1031-1038.*
Fu et al., "Enhancement of Fumaric Acid Production by Rhizopus oryzae Using a Two-stage Dissolved Oxygen Control Strategy", Applied Biochemistry and Biotechnology, 2010, vol. 162, pp. 1031-1038.
International Search Report for PCT/JP2016/088288 (PCT/ISA/210) dated Mar. 28, 2017.
Yoneya et al., "Effect of Aeration Intensity on the Production of Organic Acids and Ethanol by Rhizopus javanicus", Journal of the Agricultural Chemical Society of Japan, 1979, vol. 53, No. 11, pp. 363-367.
Hiroshi "Oxygen supply to a cultured cell," Journal of Bioscience and Bioengineering, vol. 91, No. 11, Nov. 25, 2013, pp. 646-653 (23 pages total), with machine translation and bibliographic information.

* cited by examiner

*Primary Examiner* — Heidi Reese
(74) *Attorney, Agent, or Firm* — Birch, Stewart, Kolasch & Birch, LLP

(57) ABSTRACT

The present invention provides a novel method for producing an organic acid efficiently. A method for producing an organic acid from a carbon source in a medium using a filamentous fungus, the method comprising culturing the filamentous fungus in a liquid culture medium, in which the carbon source is comprised and a dissolved oxygen concentration is controlled at 8 ppm or more and 35 ppm or less, to obtain the organic acid.

11 Claims, No Drawings

METHOD FOR PRODUCING ORGANIC ACID

FIELD OF THE INVENTION

The present invention relates to a method for producing an organic acid, and specifically relates to a method for producing fumaric acid.

BACKGROUND OF THE INVENTION

Fumaric acid is utilized for, for example, a raw material of plastic such as an alkyd resin, food additives, bath agent and intermediate materials for converting into commodity chemicals such as aspartic acid. Fumaric acid is produced industrially as petrochemicals from benzene or butane. Recently, production of fumaric acid using renewable resources is required from the viewpoint of depletion of fossil resources and an environmental issue such as global warming.

For example, a method for producing fumaric acid from saccharides by culturing a filamentous fungus such as *Rhizopus delemar* (*Rhizopus delemar*) is known as a method for producing fumaric acid using renewable resources.

In culture of a filamentous fungus, it is thought that fumaric acid is primarily produced in a reductive TCA cycle starting from pyruvic acid produced from a carbon source. On the other hand, there is a pathway to produce ethanol also from pyruvic acid, and thus the production of fumaric acid by using a filamentous fungus has a problem that ethanol is produced as a by-product. Accordingly, in order to improve production of fumaric acid, it is important to reduce production of ethanol as a by-product and increase a ratio of conversion to fumaric acid.

Examples of conventional techniques for improving a production yield of fumaric acid include a method of retaining a dissolved oxygen concentration in a culture medium at about 80 to 100% of saturation in a cell proliferation phase, and about 30 to 80% of saturation in an acid production phase in a fermentation step for producing fumaric acid by growing fungi belonging to *Rhizopus* in a culture medium including a carbon source (Patent Literature 1).

PATENT LITERATURE

Patent Literature 1: JP H3-505396 A

SUMMARY OF INVENTION

The present invention provides a method for producing an organic acid from a carbon source in a medium using a filamentous fungus, comprising culturing the filamentous fungus in a liquid culture medium, in which the carbon source is contained and a dissolved oxygen concentration is controlled at 8 ppm or more and 35 ppm or less, to obtain the organic acid.

DETAILED DESCRIPTION OF THE INVENTION

However, the present inventors found that when a step of culturing a filamentous fungus was carried out with a dissolved oxygen concentration in a medium controlled within a range of from about 30 to 80% as described in the above Patent Literature 1, that is, from about 2.1 to 5.7 ppm, a large amount of ethanol was produced, and thus a sufficient production yield of fumaric acid was not achieved in some cases.

Accordingly, the present invention relates to providing a novel method which can efficiently produce an organic acid, specifically fumaric acid.

The present inventors, after pursuing studies to improve a yield of an organic acid by using a filamentous fungus, found that by-production of ethanol from a carbon source can be reduced and ratio of conversion to an organic acid can be increased by elevating a dissolved oxygen concentration in a liquid culture medium containing a carbon source during culturing a filamentous fungus, and controlling the concentration within a predetermined range.

According to the present invention, a ratio of conversion from a carbon source to an organic acid can be increased and an organic acid can be produced in a high yield using a filamentous fungus.

The method for producing an organic acid of the present invention comprises culturing a filamentous fungus in a liquid culture medium, in which a carbon source is contained and a dissolved oxygen concentration is controlled at 8 ppm or more and 35 ppm or less, to obtain an organic acid.

In the present invention, the organic acid refers to an organic acid produced from a carbon source in a process of culturing a filamentous fungus. Examples of the organic acid include fumaric acid, lactic acid, itaconic acid, malic acid, and pyruvic acid. Specifically, the organic acid is preferably at least one selected from the group consisting of fumaric acid, pyruvic acid, lactic acid, and malic acid, more preferably at least one selected from the group consisting of fumaric acid and pyruvic acid, even more preferably fumaric acid.

(Filamentous Fungus)

Examples of the filamentous fungus used in the present invention include a microorganism belonging to *Rhizopus*, *Aspergillus*, and *Mucor*. Specific examples of the filamentous fungus include *Rhizopus delemar, Rhizopus oryzae, Aspergillus oryzae, Aspergillus niger, Aspergillus terreus,* and *Mucor mandshuricus*.

Specifically, in view of a high organic acid-producing ability, *Rhizopus* sp. is preferred, and *Rhizopus delemar* (*Rhizopus Delemer*) and *Rhizopus oryzae* are more preferred.

In the present invention, the filamentous fungus may be used in a form of a pelleted, a flocculent, a clumpy, or an immobilized filamentous fungus. The filamentous fungus may be used singly, or the fungi may be used as a mixture. As used herein, the "pelleted" filamentous fungus refers to a mycelial mass having a size of several hundreds of micrometers to several millimeters formed autonomously by a mycelium due to liquid culture. Further, the "flocculent" filamentous fungus refers to a scattered mycelium having a size of several tens of micrometers. The "clumpy" filamentous fungus refers to mycelial mass grown to a size of several tens of millimeters or more by aggregation of mycelia. The "immobilized filamentous fungus" refers to a filamentous fungus retained or embedded in a carrier.

Specifically, in view of a high organic acid-producing ability and in view of handling, a filamentous fungal pellet and an immobilized filamentous fungus are preferred, and a filamentous fungal pellet is more preferred.

Commercially available one of such a filamentous fungus may be used. Alternatively, for example, a filamentous fungal pellet or an immobilized filamentous fungus prepared by the following steps may be used.

(Step for Preparing Filamentous Fungal Pellet)

The filamentous fungal pellet can be prepared by culture.

The medium used for the culture may be any of a synthetic medium, a natural medium, and a semi-synthesized medium containing a synthetic medium supplemented with a natural ingredient, as long as the medium is a liquid culture medium which can grow a filamentous fungus. The medium generally contains, for example, a carbon source, a nitrogen source, and an inorganic salt, as described below. A composition of the ingredients can be chosen as desired.

In culture conditions, a culture temperature is, in view of growth of a filamentous fungal pellet, preferably 20° C. or more, more preferably 25° C. or more; and also preferably 40° C. or less, more preferably 30° C. or less. Further, a pH (at 25° C.) of the medium is, in view of growth of a filamentous fungal pellet, preferably 2 or more, more preferably 3 or more; and also preferably 7 or less, more preferably 6 or less.

As a culture method, a publicly-known method can be used. For example, the method includes inoculating a filamentous fungal spore into a liquid culture medium, then germinating the spore to grow to a mycelium, allowing the mycelium to form fungal cells, and pelletizing the fungal cells. The culture is generally performed under aerobic conditions.

A culture period is, in view of growth of a filamentous fungal pellet, preferably 1 day or more, more preferably 3 days or more; and also preferably 7 days or less, more preferably 6 days or less after inoculating the filamentous fungal spore into a liquid culture medium.

A culture vessel used for culture can be suitably selected from conventionally known vessels. Specifically, examples of the vessel include an aeration-agitation culture vessel, an a bubble column culture vessel, and a fluidized-bed culture vessel. Aeration conditions are, in view of growth of a filamentous fungal pellet, preferably 0.1 vvm or more, more preferably 0.3 vvm or more; and also preferably 4 vvm or less, more preferably 2 vvm or less.

After completion of the culture, the filamentous fungal pellet can be removed from the culture vessel together with the culture medium, isolated and recovered by a convenient operation such as filtration or centrifugal separation, and used in a culture step for producing an organic acid. Meanwhile, the filamentous fungal pellet can also be left in the culture vessel, and the culture step can be performed in the same culture vessel.

Further, this step can also be performed by further divided into 2 or more steps.

(Step of Preparing Immobilized Filamentous Fungus)

The immobilized filamentous fungus can be prepared by culture.

As a culture method, a publicly-known method can be used. For example, the method includes inoculating a filamentous fungal spore into a liquid culture medium containing a carrier for immobilizing the filamentous fungus, then germinating the spore to grow a mycelium, to thereby prepare an immobilized filamentous fungus from the hypha captured in the carrier. As a carrier used for immobilization, a urethane polymer, an olefinic polymer, a diene polymer, a condensation polymer, a silicone polymer, or a fluorine polymer can be used.

The carrier may have any shape including plate-like, multilayered, corrugated, tetrahedral, spherical, ribbon-like, reticular, columnar, lattice-like, and cylindrical shape.

Then, for immobilization of a filamentous fungus, a medium and a culture vessel similar to those used in preparation of the filamentous fungal pellet can be used.

Further, culture conditions similar to those described in preparation of the filamentous fungal pellet can be used.

Further, after completion of the culture, an immobilized filamentous fungus can be isolated and recovered in a similar manner to those used in preparation of the filamentous fungal pellet, and can be used in a culture step for producing an organic acid. Meanwhile, the immobilized filamentous fungus can also be left in the culture vessel, and the culture step can be performed in the same culture vessel.

Further, this step can also be performed by further divided into 2 or more steps.

(Liquid Culture Medium Containing Carbon Source)

The liquid culture medium used for producing an organic acid according to the present invention contains a carbon source.

The liquid culture medium may be any of a synthetic medium, a natural medium, or a semi-synthesized medium containing a synthetic medium supplemented with a natural ingredient.

Examples of the carbon source include glycerin, sorbitol, and saccharides. The carbon source is, in view of a high organic acid-producing ability, preferably saccharides.

Examples of the saccharides include monosaccharides, such as glucose, fructose, and xylose, and disaccharides, such as sucrose, lactose, and maltose. The saccharides may be an anhydride or a hydrate. Specifically, the carbon source is, in view of a high organic acid-producing ability, preferably glucose, fructose, xylose, sucrose, lactose, maltose, and sorbitol, more preferably glucose, fructose, xylose, sucrose, lactose, and maltose, even more preferably glucose.

A concentration of the carbon source in a liquid culture medium is, in view of a high organic acid-producing ability, preferably 1% by mass or more, more preferably 2% by mass or more, even more preferably 3% by mass or more; and also preferably 40% by mass or less, more preferably 30% by mass or less, even more preferably 20% by mass or less, even more preferably 15% by mass or less.

The liquid culture medium may contain a nitrogen source, an inorganic salt, and other necessary nutrients in addition to the carbon source. When the carbon source contains the above nutrients at a concentration appropriate for culture, the carbon source can be used solely.

Examples of the nitrogen source include nitrogen-containing compounds, such as ammonium sulfate, urea, ammonium nitrate, potassium nitrate, and sodium nitrate.

A concentration of nitrogen in a liquid culture medium is, in view of a high organic acid-producing ability, preferably 0.001% by mass or more, more preferably 0.002% by mass or more, even more preferably 0.004% by mass or more; and also preferably 0.1% by mass or less, more preferably 0.08% by mass or less, even more preferably 0.06% by mass or less.

Examples of the inorganic salt include a sulfate, a magnesium salt, and a zinc salt. Examples of the sulfate include magnesium sulfate, zinc sulfate, potassium sulfate, and sodium sulfate. Examples of the magnesium salt include magnesium sulfate, magnesium nitrate, and magnesium chloride. Examples of the zinc salt include zinc sulfate, zinc nitrate, and zinc chloride.

A concentration of sulfate ion in the liquid culture medium is, in view of a high organic acid-producing ability, preferably 0.001% by mass or more, more preferably 0.005% by mass or more, even more preferably 0.01% by mass or more; and also preferably 0.1% by mass or less, more preferably 0.08% by mass or less, even more preferably 0.04% by mass or less.

A concentration of magnesium ion in the liquid culture medium is, in view of a high organic acid-producing ability, preferably 0.001% by mass or more, more preferably 0.002% by mass or more; and also preferably 0.5% by mass or less, more preferably 0.2% by mass or less, even more preferably 0.1% by mass or less.

A concentration of zinc ion in the liquid culture medium is, in view of a high organic acid-producing ability, preferably 0.00001% by mass or more, more preferably 0.00005% by mass or more; and also preferably 0.1% by mass or less, more preferably 0.01% by mass or less, even more preferably 0.005% by mass or less.

A pH (at 35° C.) of the liquid culture medium is, in view of growth of fungal cells and a high organic acid-producing ability, preferably 2 or more, more preferably 3 or more; and also preferably 7 or less, more preferably 6 or less.

A pH (at 35° C.) of the liquid culture medium is preferably 2 to 7, more preferably 3 to 6. The pH of the medium can be controlled by using bases, such as calcium hydroxide, sodium hydroxide, calcium carbonate, and ammonia, or acids, such as sulfuric acid, and hydrochloric acid.

(Culture Method)

An organic acid can be produced by culturing a filamentous fungus in the above-described liquid culture medium. The filamentous fungus may be cultured according to commonly used culture conditions. For example, a culture temperature is, in view of growth of fungal cells and a high organic acid-, specifically fumaric acid-producing ability, preferably 20° C. or more, more preferably 30° C. or more; and also preferably 40° C. or less, more preferably 37° C. or less.

A culture vessel used for culture can be a conventionally known vessel. However, in view of a high organic acid-, specifically fumaric acid-producing ability, the vessel is preferably an aeration-agitation culture vessel, a bubble column culture vessel, and a fluidized-bed culture vessel. The culture may be batch culture, semi-batch culture, and continuous culture.

Culture period can be adjusted as desired.

In the present invention, production of an organic acid, specifically fumaric acid, is performed in a liquid culture medium in which a dissolved oxygen concentration is controlled at 8 ppm or more and 35 ppm or less.

The dissolved oxygen concentration in a liquid culture medium in a culture step is, in view of reducing by-production of ethanol and improving a yield of an organic acid, specifically fumaric acid, preferably 8.5 ppm or more, more preferably 9 ppm or more, even more preferably 12 ppm or more, even more preferably 15 ppm or more, even more preferably 28 ppm or more; and preferably 34 ppm or less, even more preferably 33 ppm or less.

The dissolved oxygen concentration in a liquid culture medium is preferably from 8.5 to 34 ppm, more preferably from 9 to 33 ppm, even more preferably from 12 to 33 ppm, even more preferably from 15 to 33 ppm, even more preferably from 28 to 33 ppm.

Then, control of a dissolved oxygen concentration in a liquid culture medium is preferably carried out along with monitoring the dissolved oxygen concentration over time. The dissolved oxygen concentration can be measured by a method described in the following Examples.

The dissolved oxygen concentration in a liquid culture medium can be controlled by, for example, aeration oxygen concentration, an aeration rate (quantity of airflow), a stirring rate, and pressure.

In the present invention, an aeration oxygen concentration refers to an oxygen concentration in gas supplied to a medium. The aeration oxygen concentration is, in view of controlling a dissolved oxygen concentration at 8 ppm or more and 35 ppm or less, 21% (volume ratio, the same applies hereinafter) or more, preferably 35% or more, more preferably 40% or more. The upper limit is preferably 100%. The aeration oxygen concentration may be changed according to culture behavior. Examples of a method for obtaining the gas with oxygen concentration of 21% or more include cryogenic separation, a PSA method (an adsorption method), and a membrane separation method.

An aeration rate (quantity of airflow) is preferably 0.1 vvm or more, more preferably 0.2 vvm or more; and also preferably 2 vvm or less, more preferably 1 vvm or less.

A stirring rate is preferably selected so that the gas supplied to the medium can be dispersed, and can be adjusted according to scale. A pressure is preferably from normal pressure to a slightly pressurized condition. When a pressure is applied, the pressure is preferably in a range of from 0 to 0.1 MPa.

When an organic acid, specifically fumaric acid is produced, the pH of the culture medium is decreased by the produced organic acid. Thus, the culture is generally continued along with neutralization using a neutralizer.

Examples of the neutralizer used for pH control include a hydroxide of an alkali metal or an alkaline-earth metal, a carbonate of an alkali metal or an alkaline-earth metal, an ammonium compound, or a combination thereof. Specifically, in view of a high organic acid-, specifically fumaric acid-producing ability, the neutralizer is sodium hydroxide, potassium hydroxide, calcium hydroxide, magnesium hydroxide, sodium carbonate, potassium carbonate, calcium carbonate, magnesium carbonate, ammonia water, ammonium carbonate, and ammonium bicarbonate; preferably sodium hydroxide, sodium carbonate, and potassium carbonate; even more preferably sodium hydroxide. The neutralizer can be used singly, or two or more neutralizers can be used in combination.

The organic acid produced may form a salt with the neutralizer to exist in a form of an organic acid salt.

As a result of the culture, an organic acid is accumulated in the medium.

With respect to the culture medium containing an organic acid, after completion of the culture, an insoluble matter, such as a microorganism, is preferably removed from the culture by an appropriate separation means, for example, centrifugal separation or membrane treatment such as microfiltration. The removal of an insoluble matter may be carried out either in the culture vessel, or outside the vessel after transferring from the vessel temporarily. On the other hand, the filamentous fungus isolated from the culture medium can be reused for the production of the organic acid.

According to the present invention, by-production of ethanol from a carbon source can be reduced, and ratio of conversion to an organic acid can be increased. Specifically, an organic acid can be produced from glucose at a ratio of conversion of 40% or more, more preferably 50% or more.

Then, the ratio of conversion to an organic acid (%) refers to a value obtained by dividing a concentration of the organic acid at completion of the culture by a concentration of glucose consumed in the production of the organic acid by the culture. A method for calculating the ratio of conversion to an organic acid is described in detail in Examples.

The culture medium containing an organic acid is concentrated as required. Then, the organic acid can be isolated and recovered from the culture medium by, for example, a crystallization method, an ion exchange method, solvent extraction, or a method including precipitating the organic acid as alkaline-earth metal salt, and then decomposing the precipitate by acidolysis.

With respect to the above described embodiments, the present invention also discloses the following production methods.

<1> A method for producing an organic acid from a carbon source in a medium using a filamentous fungus, comprising culturing the filamentous fungus in a liquid culture medium, in which the carbon source is comprised and a dissolved oxygen concentration is controlled at 8 ppm or more and 35 ppm or less, to obtain the organic acid.

<2> The method for producing an organic acid according to <1>, wherein the filamentous fungus is preferably a fungus belonging to *Rhizopus, Aspergillus,* or *Mucor,* more preferably *Rhizopus delemar, Rhizopus oryzae, Aspergillus oryzae, Aspergillus niger, Aspergillus terreus,* or *Mucor mandshuricus.*

<3> The method for producing an organic acid according to <1>, wherein the filamentous fungus is preferably *Rhizopus* sp., more preferably *Rhizopus delemar (Rhizopus Delemer),* or *Rhizopus oryzae.*

<4> The method for producing an organic acid according to any one of <1> to <3>, wherein the filamentous fungus is preferably in a form selected from the group consisting of pelleted, flocculent, clumpy, and an immobilized filamentous fungus, more preferably a filamentous fungal pellet, and an immobilized filamentous fungus, even more preferably a filamentous fungal pellet.

<5> The method for producing an organic acid according to any one of <1> to <4>, wherein the carbon source is preferably at least one selected from the group consisting of glycerin, sorbitol, and saccharides, more preferably saccharides, even more preferably at least one selected from the group consisting of glucose, fructose, xylose, sucrose, lactose, maltose, and sorbitol, even more preferably at least one selected from the group consisting of glucose, fructose, xylose, sucrose, lactose, and maltose, even more preferably glucose.

<6> The method for producing an organic acid according to any one of <1> to <5>, wherein a concentration of the carbon source in the liquid culture medium is preferably 1% by mass or more, more preferably 2% by mass or more, even more preferably 3% by mass or more; also preferably 40% by mass or less, more preferably 30% by mass or less, even more preferably 20% by mass or less, even more preferably 15% by mass or less; and also preferably from 1 to 40% by mass, more preferably from 2 to 30% by mass, even more preferably from 3 to 20% by mass, still more preferably from 3 to 20% by mass.

<7> The method for producing an organic acid according to any one of <1> to <6>, wherein the liquid culture medium preferably further comprises a nitrogen source and an inorganic salt.

<8> The method for producing an organic acid according to any one of <1> to <7>, wherein the nitrogen source is preferably ammonium sulfate, urea, ammonium nitrate, potassium nitrate, or sodium nitrate, and the inorganic salt is preferably a sulfate, a magnesium salt, or a zinc salt, more preferably magnesium sulfate, zinc sulfate, potassium sulfate, sodium sulfate, magnesium sulfate, magnesium nitrate, magnesium chloride, zinc sulfate, zinc nitrate, or zinc chloride.

<9> The method for producing an organic acid according to <7> or <8>, wherein a concentration of the nitrogen in the liquid culture medium is preferably 0.001% by mass or more, more preferably 0.002% by mass or more, even more preferably 0.004% by mass or more; also preferably 0.1% by mass or less, more preferably 0.08% by mass or less, even more preferably 0.06% by mass or less; and also preferably from 0.001 to 0.1% by mass, more preferably from 0.002 to 0.08% by mass, still more preferably from 0.004 to 0.06% by mass.

<10> The method for producing an organic acid according to <7> or <8>, wherein a concentration of sulfate ion in the liquid culture medium is preferably 0.001% by mass or more, more preferably 0.005% by mass or more, even more preferably 0.01% by mass or more; also preferably 0.1% by mass or less, more preferably 0.08% by mass or less, even more preferably 0.04% by mass or less; and also preferably from 0.001 to 0.1% by mass, more preferably from 0.005 to 0.08% by mass, even more preferably form 0.01 to 0.04% by mass.

<11> The method for producing an organic acid according to <7> or <8>, wherein a concentration of magnesium ion in the liquid culture medium is preferably 0.001% by mass or more, more preferably 0.002% by mass or more; also preferably 0.5% by mass or less, more preferably 0.2% by mass or less, even more preferably 0.1% by mass or less; and also preferably from 0.001 to 0.5% by mass, more preferably from 0.002 to 0.2% by mass, even more preferably form 0.002 to 0.1% by mass.

<12> The method for producing an organic acid according to <7> or <8>, wherein a concentration of zinc ion in the liquid culture medium is preferably 0.00001% by mass or more, more preferably 0.00005% by mass or more; also preferably 0.1% by mass or less, more preferably 0.01% by mass or less, even more preferably 0.005% by mass or less; and also preferably from 0.00001 to 0.1% by mass, more preferably from 0.00005 to 0.01% by mass, even more preferably from 0.00005 to 0.005% by mass.

<13> The method for producing an organic acid according to any one of <1> to <12>, wherein a pH (at 35° C.) of the liquid culture medium is preferably 2 or more, more preferably 3 or more; also preferably 7 or less, preferably 6 or less; and also preferably from 2 to 7, more preferably from 3 to 6.

<14> The method for producing an organic acid according to any one of <1> to <13>, wherein a culture temperature is preferably 20° C. or more, more preferably 30° C. or more; also preferably 40° C. or less, more preferably 37° C. or less; and also preferably from 20 to 40° C., more preferably from 30 to 37° C.

<15> The method for producing an organic acid according to any one of <1> to <14>, wherein the dissolved oxygen concentration in the liquid culture medium is preferably 8.5 ppm or more, more preferably 9 ppm or more, even more preferably 12 ppm or more, even more preferably 15 ppm or more, even more preferably 28 ppm or more; also preferably 34 ppm or less, still more preferably 33 ppm or less; and also preferably from 8.5 to 34 ppm, more preferably from 9 to 33 ppm, even more preferably from 12 to 33 ppm, even more preferably from 15 to 33 ppm, even more preferably from 28 to 33 ppm.

<16> The method for producing an organic acid according to any one of <1> to <15>, wherein the dissolved oxygen concentration in the liquid culture medium is controlled by preferably an aeration oxygen concentration, an aeration rate (quantity of airflow), a stirring rate, or pressure.

<17> The method for producing an organic acid according to <16>, wherein the aeration oxygen concentration is preferably 21% (volume ratio, the same applies hereinafter) or more, more preferably 35% or more, even more preferably 40% or more; also preferably 100% or less; and also preferably from 21 to 100%, more preferably from 35 to 100%, even more preferably from 40 to 100%.

<18> The method for producing an organic acid according to <16> or <17>, wherein the aeration rate (quantity of airflow) is preferably 0.1 vvm or more, more preferably 0.2 vvm or more; also preferably 2 vvm or less, more preferably 1 vvm or less; and also preferably from 0.1 to 2 vvm, more preferably from 0.2 to 1 vvm.

<19> The method for producing an organic acid according to any one of <16> to <18>, wherein the pressure is preferably from normal pressure to a slightly pressurized condition, and when pressure is applied, the pressure is preferably in a range of from 0 to 0.1 MPa.

<20> The method for producing an organic acid according to any one of <1> to <19>, wherein the organic acid is produced from glucose at a ratio of conversion of preferably 40% or more, more preferably 50% or more.

<21> The method for producing an organic acid according to any one of <1> to <20>, wherein the organic acid is at least one selected from the group consisting of fumaric acid, lactic acid, itaconic acid, malic acid, and pyruvic acid, more preferably at least one selected from the group consisting of fumaric acid, pyruvic acid, lactic acid, and malic acid, even more preferably at least one selected from the group consisting of fumaric acid and pyruvic acid, even more preferably fumaric acid.

EXAMPLES

<Analysis Method>

[Measurement of Each Ingredient by High Performance Liquid Chromatography (HPLC)]

A culture medium was appropriately diluted with an 0.0085 N aqueous sulfuric acid solution, and filtered using a cellulose acetate membrane filter with pore size of 0.22 μm (manufactured by ADVANTEC Co., Ltd.) to provide a sample for HPLC analysis. Conditions for HPLC analysis were as follows.

Column: ICSep ICE-ION-300
Eluant: 0.0085 N sulfuric acid, 0.4 mL/min
Detection method i: RI (HITACHI, L-2490)
Detection method ii: UV (HITACHI, L-2455, measurement wavelength: 250 nm)
Column temperature: 40° C.
Injection volume: 20 μL
Retention time: 40 min Retention time of each ingredient in this analysis system was as follows.

Pyruvic acid: 15 min
Glucose: 16 min
Fumaric acid: 26 min
Ethanol: 34 min

[Measurement of Dissolved Oxygen Concentration]

A dissolved oxygen concentration in a culture medium was measured using a DO sensor (O24100e) manufactured by METTLER TOLEDO.

<Preparation of Filamentous Fungal Pellet>

[Preparation of Spore Suspension]

Fungal strains used were filamentous fungi *Rhizopus delemar* JCM5557 and NBRC5441 strains obtained from an Incorporated Administrative Agency of National Institute of Technology and Evaluation (NITE). Fungal cells of each filamentous fungus were separately streaked and applied to a slant agar medium (Difco Potato Dextrose Agar, Becton, Dickinson and Company) formed in a test tube, cultured statically at 30° C., and subcultured regularly. In order to use the fungal cells, 10 mL of sterilized distilled water was added to the test tube in which fungal cells were grown, then stirred for 4 minutes using a touch mixer to recover spores. Then, the spores were diluted to adjust to $1 \times 10^6$ spores/mL by adding aseptic distilled water, and used as a spore suspension.

[Pelletizing Filamentous Fungus]

Preparation of a filamentous fungal pellet was carried out by the following two-step culture.

First step of the culture was performed as follows. A 500 mL baffled Erlenmeyer flask containing 200 mL of a PDB medium (Difco Potato Dextrose Broth, Becton, Dickinson and Company) was sterilized, and then a spore suspension prepared by the above-described method was inoculated to make $1 \times 10^4$ spores/mL and cultured for 3 days under culture conditions at pH of in a range from 3 to 6 at 27° C. with stirring at 170 r/min (PRECI CO., LTD., PRXYg-98R).

Second step of the culture was performed as follows. A 1 L aeration-agitation vessel containing 500 mL of a pellet forming medium (10% by mass of glucose (manufactured by Wako Pure Chemical Industries, Ltd.), 0.025% by mass of magnesium sulfate heptahydrate, 0.009% by mass of zinc sulfate heptahydrate, 0.1% by mass of ammonium sulfate, and 0.06% by mass of potassium dihydrogenphosphate) was sterilized, and then fungal cells in an amount of 500 mL of the culture medium of the first step was inoculated and cultured for 2 days under conditions at 27° C. with stirring at 500 r/min with supply of air at an aeration rate of 0.3 vvm. The pH was adjusted by adding 7 N sodium hydroxide solution adequately to maintain a pH (at 27° C.) of 4.0.

[Recovery of Pellet]

The culture medium of the filamentous fungal pellet obtained in each of the above-described steps was filtered using a nylon mesh filter for several tens of seconds until dripping of filtrate was mostly stopped to obtain a wet filamentous fungal pellet. The pellet obtained in the second step was immediately subjected to the following culture step.

<Producing Organic Acid>

[Culture Method]

Example 1

To a 1 L aeration-agitation vessel, 500 mL of a liquid culture medium (composition: 10% by mass of glucose (manufactured by Wako Pure Chemical Industries, Ltd.), 0.025% by mass of magnesium sulfate heptahydrate, 0.009% by mass of zinc sulfate heptahydrate, 0.1% by mass of ammonium sulfate) was added, and then whole of the filamentous fungal pellet of JCM5557 (in wet condition) prepared above was added. Immediately afterwards, sampling at time 0 of the culture was carried out, and then stirring culture was performed with aeration of gas with an oxygen concentration of 100% produced by an oxygen generator (AIR SEP CORPORATION, NEWLIFE J) under conditions at temperature of 35° C. with stirring at 500 r/min at an aeration rate of 0.3 vvm for 2 days while sampling over time.

During the culture, the dissolved oxygen concentration in the culture medium was 32 ppm. Further, during the culture, the pH of the culture medium was adjusted by adding 7 N sodium hydroxide solution adequately to maintain a pH (at 35° C.) of 4.0. After completion of the culture, the fungal cells were removed by filtering the culture medium to obtain a fumaric acid-containing culture medium.

Example 2

A fumaric acid-containing culture medium was obtained by culturing in the same manner as Example 1, except that the aeration oxygen concentration was modified to be 50% by mixing the gas produced by an oxygen generator (AIR SEP CORPORATION, NEWLIFE J) with air. During the culture, the dissolved oxygen concentration in the culture medium was 9.5 ppm.

Example 3

A fumaric acid-containing culture medium was obtained by culturing in the same manner as Example 1, except that the aeration oxygen concentration was modified to be 35% by mixing the gas produced by an oxygen generator (AIR SEP CORPORATION, NEWLIFE J) with air. During the culture, the dissolved oxygen concentration in the culture medium was 8.0 ppm.

Comparative Example 1

A fumaric acid-containing culture medium was obtained in the same manner as Example 1, except that the gas used in the aeration was replaced with air (aeration oxygen concentration: 21%). During the culture, the dissolved oxygen concentration in the culture medium was 5.4 ppm.

Example 4

To a 1 L aeration-agitation vessel, 500 mL of a liquid culture medium (composition: 3% by mass of glucose (manufactured by Wako Pure Chemical Industries, Ltd.), 0.025% by mass of magnesium sulfate heptahydrate, 0.009% by mass of zinc sulfate heptahydrate, 0.1% by mass of ammonium sulfate) was added, and then whole of the filamentous fungal pellet of NBRC5441 (in wet condition) prepared above was added. Immediately afterwards, sampling at time 0 of the culture was carried out, and then stirring culture was performed with aeration of gas with an oxygen concentration of 100% produced by an oxygen generator (AIR SEP CORPORATION, NEWLIFE J) under conditions at temperature of 35° C. with stirring at 500 r/min at an aeration rate of 0.3 vvm for 2 days while sampling over time. During the culture, the dissolved oxygen concentration in the culture medium was 28 ppm. Further, during the culture, the pH of the culture medium was adjusted by adding 7 N sodium hydroxide solution adequately to maintain a pH (at 35° C.) of 3.0. After completion of the culture, the fungal cells were removed by filtering the culture medium to obtain an organic acid-containing culture medium.

Comparative Example 2

An organic acid-containing culture medium was obtained in the same manner as Example 4, except that the gas used in the aeration was replaced with air (aeration oxygen concentration: 21%). During the culture, the dissolved oxygen concentration in the culture medium was 5.0 ppm.

Example 5

To a 1 L aeration-agitation vessel, 500 mL of a liquid culture medium (composition: 3% by mass of glucose (manufactured by Wako Pure Chemical Industries, Ltd.), 0.025% by mass of magnesium sulfate heptahydrate, 0.009% by mass of zinc sulfate heptahydrate, 0.1% by mass of ammonium sulfate) was added, and then whole of the filamentous fungal pellet of NBRC5441 (in wet condition) prepared above was added. Immediately afterwards, sampling at time 0 of the culture was carried out, and then stirring culture was performed with aeration of gas with an oxygen concentration of 100% produced by an oxygen generator (AIR SEP CORPORATION, NEWLIFE J) under conditions at temperature of 35° C. with stirring at 500 r/min at an aeration rate of 0.3 vvm for 2 days while sampling over time. During the culture, the dissolved oxygen concentration in the culture medium was 28 ppm. Further, during the culture, the pH of the culture medium was adjusted by adding 7 N sodium hydroxide solution adequately to maintain a pH (at 35° C.) of 7.0. After completion of the culture, the fungal cells were removed by filtering the culture medium to obtain an organic acid-containing culture medium.

Comparative Example 3

An organic acid-containing culture medium was obtained by culturing in the same manner as Example 5, except that the aeration oxygen concentration was modified to be 21% by mixing the gas produced by an oxygen generator (AIR SEP CORPORATION, NEWLIFE J) with air. During the culture, the dissolved oxygen concentration in the culture medium was 5.0 ppm.

Example 6

To a 1 L sterilized aeration-agitation vessel, 500 mL of a liquid culture medium (composition: 5% by mass of mixed saccharides (glucose:fructose:sucrose:xylose:lactose:maltose=5:5:2:1:1:1, mixing ratio), 0.025% by mass of magnesium sulfate heptahydrate, 0.009% by mass of zinc sulfate heptahydrate, 0.1% by mass of ammonium sulfate) was added, and then whole of the filamentous fungal pellet of JCM5557 (in wet condition) prepared above was added. Immediately afterwards, sampling at time 0 of the culture was carried out, and then stirring culture was performed with aeration of gas with an oxygen concentration of 100% produced by an oxygen generator (AIR SEP CORPORATION, NEWLIFE J) under conditions at temperature of 35° C. with stirring at 500 r/min at an aeration rate of 0.3 vvm for 2 days while sampling over time. During the culture, the dissolved oxygen concentration in the culture medium was 30 ppm. Further, during the culture, the pH of the culture medium was adjusted by adding 7 N sodium hydroxide solution adequately to maintain a pH (at 35° C.) of 4.0. After completion of the culture, the fungal cells were removed by filtering the culture medium to obtain an organic acid-containing culture medium.

Comparative Example 4

An organic acid-containing culture medium was obtained by culturing in the same manner as Example 6, except that the aeration oxygen concentration was modified to be 21% by mixing the gas produced by an oxygen generator (AIR SEP CORPORATION, NEWLIFE J) with air. During the culture, the dissolved oxygen concentration in the culture medium was 5.0 ppm.

[Method for Evaluation]

In values obtained by analysis of the culture medium, the following items (1) to (6) were defined as targets of evaluation. Formulas for calculating the items are shown in Table 1 and equations (1) to (6), respectively.

TABLE 1

| Concentration of each component [g/L] | | Symbol |
|---|---|---|
| | Glucose (Glc) | G |
| | Mixed saccharides (Mix) | M |
| | Fumaric acid (FA) | F |
| | Pyruvic acid (PyA) | Py |
| | Ethanol (EtOH) | E |

(1) Ratio of Conversion from Saccharide to Fumaric Acid $$P1[\%]=(F-F0)/(G0-G)\times100 \qquad (1)$$

(2) Ratio of Conversion from Saccharide to Ethanol $$Q[\%](E-E0)/(G0-G)\times100 \qquad (2)$$

(3) Ratio of Conversion to Carbon Dioxide Produced in the Above-Mentioned Ethanol Conversion $$R[\%]=Q\times(\text{molecular weight of }CO_2/\text{molecular weight of EtOH})\times100 \qquad (3)$$

(4) Ratio of Conversion from Saccharide to Pyruvic Acid $$S1[\%]=(Py-Py0)/(G0-G)\times100 \qquad (4)$$

(5) Ratio of Conversion from Mixed Saccharides to Fumaric Acid $$P2[\%](F-F0)/(M0-M)\times100 \qquad (5)$$

(6) Ratio of Conversion from Mixed Saccharides to Pyruvic Acid $$S2[\%]=(Py-Py0)/(M0-M)\times100 \qquad (6)$$

In the equations, G0, M0, F0, E0, and Py0 represent a concentration of glucose, a concentration of the mixed saccharides, a concentration of fumaric acid, a concentration of ethanol, and a concentration of pyruvic acid at time 0 of culture, respectively. G, M, F, E, and Py represent a concentration of glucose, a concentration of the mixed saccharides, a concentration of fumaric acid, a concentration of ethanol, and a concentration of pyruvic acid after completion of culture, respectively.

Conditions and Results of the Examples and Comparative Examples are shown in Table 2 to Table 4.

TABLE 2

| | Example 1 | Example 2 | Example 3 | Comparative Example 1 |
|---|---|---|---|---|
| Dissolved oxygen concentration | 32 ppm | 9.5 ppm | 8.0 ppm | 5.4 ppm |
| pH of culture medium | 4.0 | 4.0 | 4.0 | 4.0 |
| Conversion ratio to fumaric acid | 65.7% | 50.7% | 42.4% | 36.9% |
| Conversion ratio to ethanol | 9.9% | 17.2% | 16.1% | 20.6% |
| Conversion ratio to $CO_2$ | 9.4% | 16.5% | 15.4% | 19.7% |

TABLE 3

| | Example 4 | Comparative Example 2 | Example 5 | Comparative Example 3 |
|---|---|---|---|---|
| Dissolved oxygen concentration | 28 ppm | 5.0 ppm | 30 ppm | 5.0 ppm |
| pH of culture medium | 3.0 | 3.0 | 7.0 | 7.0 |
| Conversion ratio to fumaric acid | 51.0% | 30.0% | 58.2% | 41.4% |
| Conversion ratio to Pyruvic acid | 42.5% | 9.5% | 4.1% | 0.1% |
| Conversion ratio ro ethanol | 2.2% | 19.2% | 0.0% | 12.9% |
| Conversion ratio to $CO_2$ | 2.1% | 18.4% | 0.0% | 12.3% |

TABLE 4

| | Example 6 | Comparative Example 4 |
|---|---|---|
| Dissolved oxygen concentration | 30 ppm | 5.0 ppm |
| pH of culture medium | 4.0 | 4.0 |
| Conversion ratio to fumaric acid | 39.0% | 30.0% |
| Conversion ratio to Pyruvic acid | 21.2% | 4.5% |
| Conversion ratio to ethanol | 2.8% | 11.4% |
| Conversion ratio to $CO_2$ | 2.7% | 10.9% |

As shown in Table 2 to Table 4, it was found that conversion from glucose or a mixed saccharides to fumaric acid and pyruvic acid was promoted by controlling a dissolved oxygen concentration in a culture medium within a range of the present invention in a culture step of a filamentous fungus, whereas by-production of ethanol was reduced, and thus an organic acid was obtained in high yield.

In Comparative Examples 1 to 4 in which normal air (atmospheric gases) was supplied, a large amount of ethanol was produced as a by-product, and thus an organic acid was obtained in low yield.

The invention claimed is:

1. A method for producing fumaric acid from a carbon source comprising saccharides in a medium using a filamentous fungus, the method comprising culturing the filamentous fungus in a liquid culture medium, in which the carbon source is comprised and a dissolved oxygen concentration is controlled at 8 ppm or more and 35 ppm or less, to obtain the fumaric acid.

2. The method for producing fumaric acid according to claim 1, wherein the filamentous fungus is *Rhizopus* sp.

3. The method for producing fumaric acid according to claim 1, wherein the filamentous fungus is *Rhizopus delemar* or *Rhizopus oryzae*.

4. The method for producing fumaric acid according to claim 1, wherein the filamentous fungus is in a form of a pelleted or an immobilized filamentous fungus.

5. The method for producing fumaric acid according to claim 1, wherein the liquid culture medium is a liquid culture medium in which a dissolved oxygen concentration is controlled at 8.5 ppm or more.

6. The method for producing fumaric acid according to claim 1, wherein the liquid culture medium is aerated with a gas with an oxygen concentration of greater than or equal to 21% and less than or equal to 100%.

7. The method for producing fumaric acid according to claim 1, wherein the carbon source comprises glucose.

8. The method for producing fumaric acid according to claim 1, wherein a concentration of the carbon source in the liquid culture medium is greater than or equal to 1 mass % and less than or equal to 40 mass %.

9. The method for producing fumaric acid according to claim 1, wherein a pH at 35° C. of the liquid culture medium in the culture step is greater than or equal to 2 and less than or equal to 7.

10. The method for producing fumaric acid according to claim 1, wherein a pH at 35° C. of the liquid culture medium in the culture step is greater than or equal to 3 and less than or equal to 6.

11. The method for producing fumaric acid according to claim 1, wherein the pH of the liquid culture medium in the culture step is adjusted using a hydroxide of an alkali metal or an alkaline earth metal, or a carbonate of an alkali metal or an alkaline earth metal.

* * * * *